US012708264B2

(12) United States Patent
Lee

(10) Patent No.: US 12,708,264 B2
(45) Date of Patent: Aug. 18, 2026

(54) METHOD FOR DETERMINING STRUCTURAL PROGRESSION OF EYE DISEASE AND DEVICE THEREOF

(71) Applicant: IUCF-HYU (INDUSTRY-UNIVERSITY COOPERATION FOUNDATION HANYANG UNIVERSITY), Seoul (KR)

(72) Inventor: Won June Lee, Seoul (KR)

(73) Assignee: IUCF-HYU (INDUSTRY-UNIVERSITY COOPERATION FOUNDATION HANYANG UNIVERSITY), Seoul (KR)

( * ) Notice: Subject to any disclaimer, the term of this patent is extended or adjusted under 35 U.S.C. 154(b) by 1004 days.

(21) Appl. No.: 17/779,851

(22) PCT Filed: Nov. 3, 2020

(86) PCT No.: PCT/KR2020/015219

§ 371 (c)(1),
(2) Date: May 25, 2022

(87) PCT Pub. No.: WO2021/107433

PCT Pub. Date: Jun. 3, 2021

(65) Prior Publication Data

US 2023/0000347 A1 Jan. 5, 2023

(30) Foreign Application Priority Data

Nov. 27, 2019 (KR) ........................ 10-2019-0154909

(51) Int. Cl.
*A61B 3/12* (2006.01)
*A61B 3/00* (2006.01)
*A61B 3/14* (2006.01)

(52) U.S. Cl.
CPC .................. *A61B 3/12* (2013.01); *A61B 3/00* (2013.01); *A61B 3/1233* (2013.01); *A61B 3/14* (2013.01)

(58) Field of Classification Search
CPC ........... A61B 3/12; A61B 3/14; A61B 3/0025; A61B 5/00; G16H 50/20
See application file for complete search history.

(56) References Cited

U.S. PATENT DOCUMENTS 9,117,121 B2 * 8/2015 Leung .................. G06T 7/0016
2010/0302507 A1 * 12/2010 Desgroseilliers ........ A61B 3/14 351/246
2018/0096479 A1 * 4/2018 Iwase .................. A61B 3/0041

FOREIGN PATENT DOCUMENTS

KR 10-2013-0000576 A 1/2013
KR 10-2016-0045216 A 4/2016
(Continued)

OTHER PUBLICATIONS

Korean Notification of Reason for Refusal for 10-2019-0154909 dated, Dec. 23, 2020.
(Continued)

*Primary Examiner* — Peter K Huntsinger
(74) *Attorney, Agent, or Firm* — Sughrue Mion, PLLC

(57) ABSTRACT

The present invention relates to a method and a device for determining structural progression of an eye disease using an ocular image. According to an embodiment of the present invention, a device for determining structural progression of an eye disease includes a processor, and a memory electrically connected to the processor, wherein, when the processor is executed, the memory stores instructions for obtaining a first-n$^{th}$ ocular image, which is an n$^{th}$ first ocular image for a user (where n is a natural number), obtaining a second-n$^{th}$ ocular image, which is an n$^{th}$ second ocular image for the user, combining the first-n$^{th}$ ocular image and the second-n$^{th}$
(Continued)

ocular image according to a preset method to generate an $n^{th}$ combined image, and generating an $n^{th}$ eye disease image for the user by using the $n^{th}$ combined image and a preset prone area image.

12 Claims, 8 Drawing Sheets

(56) References Cited

FOREIGN PATENT DOCUMENTS

| | | | |
|---|---|---|---|
| KR | 10-1637314 | B1 | 7/2016 |
| KR | 10-2019-0087272 | A | 7/2019 |
| KR | 10-2032047 | B1 | 10/2019 |

OTHER PUBLICATIONS

International Search Report for PCT/KR2020/015219 dated, Feb. 8, 2021 (PCT/ISA/210).

* cited by examiner

700

METHOD FOR DETERMINING STRUCTURAL PROGRESSION OF EYE DISEASE AND DEVICE THEREOF

CROSS REFERENCE TO RELATED APPLICATIONS

This application is a National Stage of International Application No. PCT/KR2020/015219, filed on Nov. 3, 2020, the contents of which are incorporated herein by reference in their entireties.

TECHNICAL FIELD

The present invention relates to a method and a device for determining structural progression of an eye disease using an ocular image.

BACKGROUND ART

Glaucoma is an optic nerve disorder due to an increase in intraocular pressure, resulting in visual field loss and visual loss, and is a very dangerous and frequent disease from among ophthalmic diseases. Glaucoma, along with cataract and macular degeneration, is one of the three major blindness-causing ophthalmic diseases. Because of the chronic and irreversible nature of glaucoma, early detection of glaucoma can be delayed through treatment or surgery, and the therapeutic effect is good.

Currently, there are various methods of diagnosing glaucoma, such as scanning laser polarimetry (SLP) or optical coherence tomography (OCT), visual field test, and comparison of a depression ratio of optic disc (OD).

In particular, in the case of optical coherence tomography (OCT), the spatial relationship between the optic disc and the macula related to glaucoma progression is difficult to grasp because the optic disc and the macula are photographed separately and the results are analyzed separately.

DESCRIPTION OF EMBODIMENTS

Technical Problem

The present invention provides a method and a device capable of determining the structural progression of an eye disease by combining ocular images of various areas.

Solution to Problem

According to an aspect of the disclosure, a device for determining structural progression of an eye disease comprises a processor and a memory electrically connected to the processor, when the processor is executed, the memory stores instructions for obtaining a first-$n^{th}$ ocular image, which is an $n^{th}$ first ocular image for a user (where n is a natural number), obtaining a second-$n^{th}$ ocular image, which is an $n^{th}$ second ocular image for the user, combining the first-$n^{th}$ ocular image and the second-$n^{th}$ ocular image according to a preset method to generate an $n^{th}$ combined image, and generating an $n^{th}$ eye disease image for the user by using the $n^{th}$ combined image and a preset prone area image.

According to an exemplary embodiment, the memory stores instructions for generating a first-$n^{th}$ comparison image by using an optic nerve thickness of the first-$n^{th}$ ocular image and a pre-stored first-$(n-1)^{th}$ ocular image, generating a second-$n^{th}$ comparison image by using an optic nerve thickness of the second-$n^{th}$ ocular image and a pre-stored second-$(n-1)^{th}$ ocular image, and generating the $n^{th}$ combined image by combining the first-$n^{th}$ comparison image and the second-$n^{th}$ comparison image according to a preset method.

According to an exemplary embodiment, the memory stores instructions for generating the $n^{th}$ combined image by matching a blood vessel portion of the first-$n^{th}$ comparison image and a blood vessel portion of the second-$n^{th}$ comparison image.

According to an exemplary embodiment, the memory stores instructions for generating an $n^{th}$ eye disease progression image for the user using pre-stored first to n-1 combined images and the $n^{th}$ combined image, and generating the $n^{th}$ eye disease image by combining the $n^{th}$ eye disease progression image and the prone area image.

According to an exemplary embodiment, the memory stores instructions for, when an eye disease progression image of another person corresponding to the $n^{th}$ eye disease progression image is searched, analyzing the degree of eye disease progression of the user using the eye disease progression image of another person.

According to an exemplary embodiment, the memory stores instructions for searching for the eye disease progression image of another person considering a generation period and an optic nerve change position corresponding to the $n^{th}$ eye disease image, the generation period corresponds to a generation period of a first eye disease image to the $n^{th}$ eye disease image, the optic nerve change position corresponds to an optic nerve change position of each of the pre-stored first combined image to the $n^{th}$ combined image, the first eye disease image is a first image of eye disease of the user, and the first combined image is a first combined image of the user.

According to an aspect of the disclosure, a method of determining structural progression of an eye disease performed in a device for determining structural progression of an eye disease comprises: obtaining a first-$n^{th}$ ocular image, which is an $n^{th}$ first ocular image for a user (where n is a natural number), obtaining a second-$n^{th}$ ocular image, which is an $n^{th}$ second ocular image for the user, generating an $n^{th}$ combined image by combining the first-$n^{th}$ ocular image and the second-$n^{th}$ ocular image according to a preset method, and generating an $n^{th}$ eye disease image for the user by using the $n^{th}$ combined image and a preset prone area image.

According to an exemplary embodiment, the generating of the $n^{th}$ combined image comprises generating a first-$n^{th}$ comparison image by using an optic nerve thickness of the first-$n^{th}$ ocular image and a pre-stored first-$(n-1)^{th}$ ocular image, generating a second-$n^{th}$ comparison image by using an optic nerve thickness of the second-$n^{th}$ ocular image and a pre-stored second-$(n-1)^{th}$ ocular image, and generating the $n^{th}$ combined image by combining the first-$n^{th}$ comparison image and the second-$n^{th}$ comparison image according to a preset method.

According to an exemplary embodiment, the generating of the $n^{th}$ combined image comprises generating the $n^{th}$ combined image by matching a blood vessel portion of the first-$n^{th}$ comparison image and a blood vessel portion of the second-$n^{th}$ comparison image.

According to an exemplary embodiment, the generating of the $n^{th}$ eye disease image comprises generating an $n^{th}$ eye disease progression image for the user using pre-stored first to n-1 combined images and the $n^{th}$ combined image, and generating the $n^{th}$ eye disease image by combining the $n^{th}$ eye disease progression image and the prone area image.

According to an exemplary embodiment, the method further comprises: when an eye disease progression image of another person corresponding to the $n^{th}$ eye disease progression image is searched, analyzing the degree of eye disease progression of the user using the eye disease progression image of another person.

According to an exemplary embodiment, the analyzing of the degree of eye disease progression of the user comprises searching for the eye disease progression image of another person considering a generation period and an optic nerve change position corresponding to the $n^{th}$ eye disease progression image, the generation period corresponds to a generation period of a first eye disease progression image to the $n^{th}$ eye disease progression image, the optic nerve change position corresponds to an optic nerve change position of each of a first combined image to the $n^{th}$ combined image, the first eye disease progression image is a first eye disease progression image of the user, and the first combined image is a first combined image of the user.

Advantageous Effects of Disclosure

According to the present invention, since ocular images of various areas, such as the macular area and the optic nerve area, can be combined and provided as one ocular image, it is possible for an administrator to grasp the structural progression of an eye disease at a glance.

BRIEF DESCRIPTION OF DRAWINGS

A brief description of each drawing is provided to fully understand drawings recited in the detailed description of the present invention.

BEST MODE

Exemplary embodiments according to the inventive concept of the present invention are provided to more completely explain the inventive concept of the present invention to one of ordinary skill in the art, and the following embodiments may be modified in various other forms and the scope of the inventive concept of the present invention is not limited to the following embodiments. Rather, these embodiments are provided so that the present invention will be thorough and complete, and will fully convey the inventive concept of the present invention to one of ordinary skill in the art.

It will be understood that, although the terms first, second, etc. may be used herein to describe various members, regions, layers, sections, and/or components, these members, regions, layers, sections, and/or components should not be limited by these terms. These terms do not denote any order, quantity, or importance, but rather are only used to distinguish one component, region, layer, and/or section from another component, region, layer, and/or section. Thus, a first member, component, region, layer, or section discussed below could be termed a second member, component, region, layer, or section without departing from the teachings of the inventive concept of the present invention. For example, as long as within the scope of the present invention, a first component may be named as a second component, and a second component may be named as a first component.

Unless otherwise defined, all terms (including technical and scientific terms) used herein have the same meaning as commonly understood by one of ordinary skill in the art to which the inventive concept of the present invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As used herein, the term "and/or" includes any and all combinations of one or more of the associated listed items.

Hereinafter, embodiments of the inventive concept will be described in detail with reference to the accompanying drawings.

Figure 1:
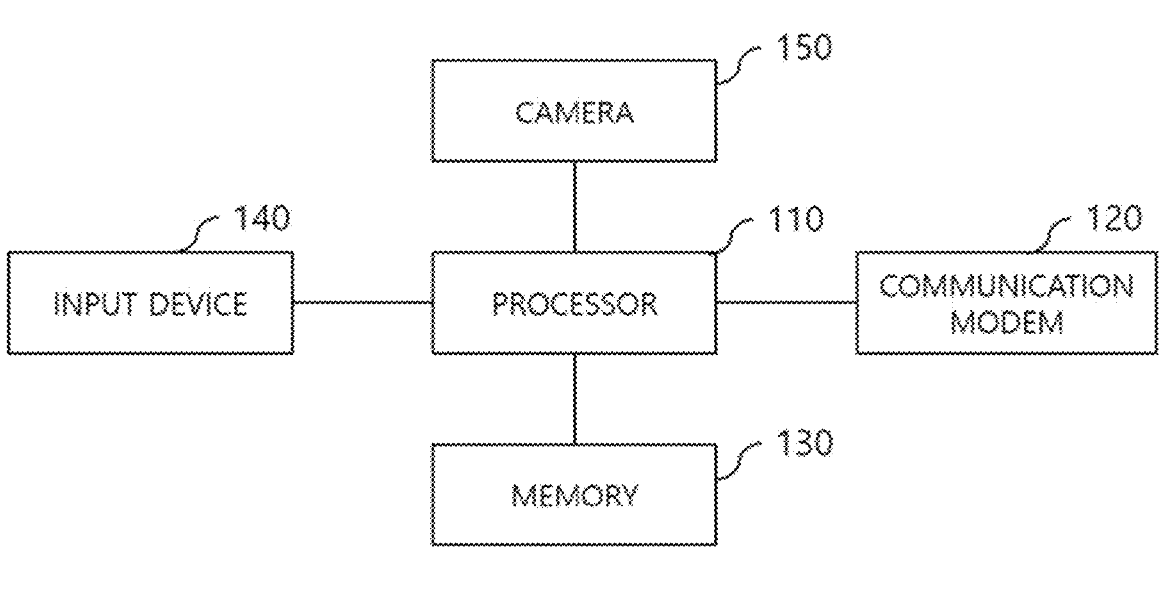
FIG. 1 is a block diagram of a device for determining the structural progression of an eye disease according to an embodiment of the present invention.

FIG. 1 is a block diagram of a device for determining the structural progression of an eye disease according to an embodiment of the present invention.

Referring to FIG. 1, a device 100 for determining the structural progression of an eye disease according to an embodiment of the present invention may be a device capable of generating a fundus image by photographing the user's eye and analyzing the fundus image. Alternatively, the device 100 for determining the structural progression of an eye disease may be a device capable of receiving and analyzing a fundus image generated by another device. The device 100 for determining the structural progression of an eye disease may include a processor 110, a communication modem 120, a memory 130, an input device 140, and/or a camera 150.

The device 100 for determining the structural progression of an eye disease may analyze the degree of progression of an eye disease (e.g., glaucoma) by analyzing a plurality of fundus images (fundus images of the same user) generated with a time difference. That is, instructions and/or information for analyzing a user's fundus image may be stored in the memory 130, and the processor 110 may access the memory 130 and execute the corresponding instructions and/or information to analyze user's eye disease progression information. Hereinafter, an analysis operation of the device 100 for determining the structural progression of an eye disease will be described in detail with reference to FIGS. 2 to 8.

Figure 2:
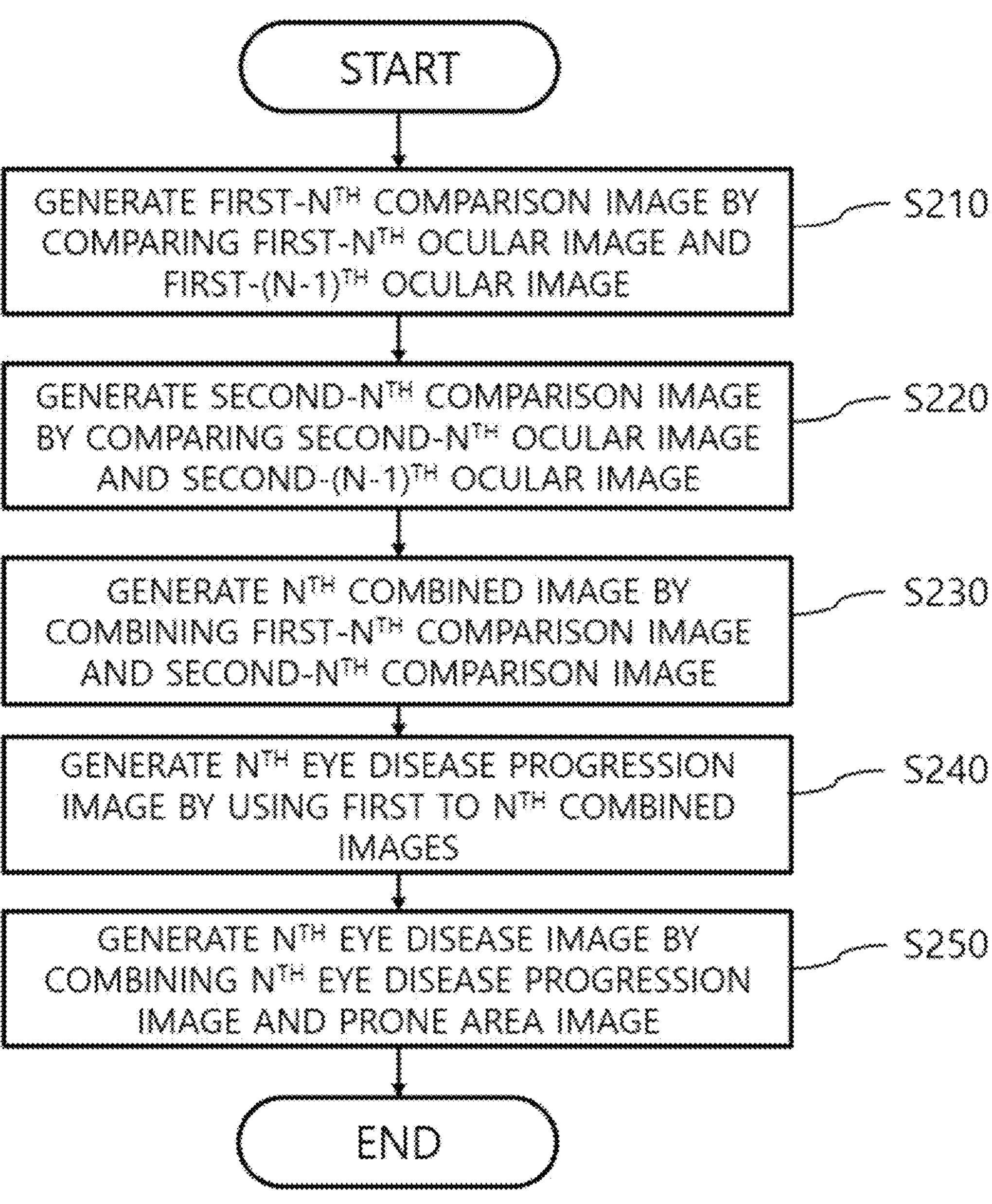
FIG. 2 is a flowchart illustrating a method of determining the structural progression of an eye disease according to an embodiment of the present invention.

FIG. 2 is a flowchart illustrating a method of determining the structural progression of an eye disease according to an embodiment of the present invention.

Before describing the method of determining the structural progression of an eye disease according to an embodiment of the present invention with reference to FIG. 2, terms to be used below are defined.

First, an ocular image may be an image of the user's eyeball generated through optical coherence tomography (OCT).

In addition, a first ocular image may be an ocular image obtained by photographing a user's optic disc. In addition, a first-$n^{th}$ ocular image may be an $n^{th}$ first ocular image from among a plurality of first ocular images photographed with a time difference (where n is a natural number).

In addition, a second ocular image may be an ocular image in which the user's macula (yellow spot) is photographed. In addition, a second-$n^{th}$ ocular image may be an $n^{th}$ second ocular image from among a plurality of second ocular images photographed with a time difference.

In addition, a first comparison image may be an image in which different portions are emphasized by comparing a plurality of first ocular images generated with a time difference (e.g., expressed by different colors of different portions). In addition, a first-$n^{th}$ comparison image may be an image generated by comparing the first-$n^{th}$ ocular image with a first-$(n-1)^{th}$ ocular image, and emphasizing different portions. The first-$(n-1)^{th}$ ocular image may be a first ocular image generated immediately before the first-$n^{th}$ ocular image.

In addition, a second comparison image may be an image in which different portions are emphasized by comparing a plurality of second ocular images generated with a time difference (e.g., expressed by different colors of different portions). In addition, a second-$n^{th}$ comparison image may be an image generated by comparing the second-$n^{th}$ ocular image with a second-$(n-1)^{th}$ ocular image, and emphasizing different portions. The second-$(n-1)^{th}$ ocular image may be a second ocular image generated immediately before the second-$n^{th}$ ocular image.

In addition, an $n^{th}$ combined image may be an image generated by combining the first-$n^{th}$ comparison image and the second-$n^{th}$ comparison image according to a preset method. A detailed description of the method of generating the $n^{th}$ combined image will be described later.

In addition, an $n^{th}$ eye disease progression image may be an image generated by combining first to $n^{th}$ combined images into one image according to a preset method. A detailed description of a method of generating the $n^{th}$ eye disease progression image will be described later.

In addition, an $n^{th}$ eye disease image may be an image generated by combining a first eye disease progression image and a preset prone area image into one image according to a preset method. A detailed description of a method of generating the $n^{th}$ eye disease image will be described later.

In operation S210, the processor 110 may generate the first-$n^{th}$ comparison image by comparing the first-$n^{th}$ ocular image and the first-$(n-1)^{th}$ ocular image. The first-$n^{th}$ ocular image may be an image photographed by the camera 150. In this case, the camera 150 may be a camera capable of optical coherence tomography (OCT). Alternatively, the first-$n^{th}$ ocular image may be an image generated by another device capable of optical coherence tomography (OCT) and received through the communication modem 120. In this case, the communication modem 120 may be a modem that can connect to the Internet, a mobile network, etc., or a USB communication port. In addition, the first-$(n-1)^{th}$ ocular image may be previously stored in the memory 130.

In addition, the processor 110 may compare the first-$n^{th}$ ocular image and the first-$(n-1)^{th}$ ocular image, and may generate a first-$n^{th}$ comparison image by changing colors of different portions as a result of the comparison (i.e., portions of the first ocular images with different thicknesses of an optic nerve).

In operation S220, the processor 110 may generate a second-$n^{th}$ comparison image by comparing the second-$n^{th}$ ocular image and the second-$(n-1)^{th}$ ocular image. The second-$n^{th}$ ocular image may be an image photographed by the camera 150. In this case, the camera 150 may be a camera capable of optical coherence tomography (OCT). Alternatively, the second-$n^{th}$ ocular image may be an image generated by another device capable of OCT and received through the communication modem 120. In addition, the processor 110 may compare the second-$n^{th}$ ocular image and the second-$(n-1)^{th}$ ocular image, and may generate a second-$n^{th}$ comparison image by changing colors of different portions as a result of the comparison (i.e., portions of the second ocular images with different thicknesses of the optic nerve).

In operation S230, the processor 110 may generate an $n^{th}$ combined image by combining the first-$n^{th}$ comparison image and the second-$n^{th}$ comparison image according to a preset method. The processor 110 may detect a blood vessel portion in the first-$n^{th}$ comparison image. In addition, the processor 110 may detect a blood vessel portion in the second-$n^{th}$ comparison image. Accordingly, the processor 110 may generate the $n^{th}$ combined image by matching blood vessel portions of the first-$n^{th}$ comparison image and the second-$n^{th}$ comparison image. Since there are arteries, veins, and capillaries in the eye, the processor 110 may generate an $n^{th}$ combined image by separating them from each other and matching the corresponding blood vessel portions. A specific method of the processor 110 to generate the $n^{th}$ combined image by matching the blood vessel portions of the first-$n^{th}$ comparison image and the second-$n^{th}$ comparison image is similar to a known technique, and thus a detailed description thereof will be omitted.

In operation S240, the processor 110 may generate an $n^{th}$ eye disease progression image by combining the first to $n^{th}$ combined images according to a preset method. The $n^{th}$ eye disease progression image will be described later with reference to FIGS. 4 and 5.

Figure 4:
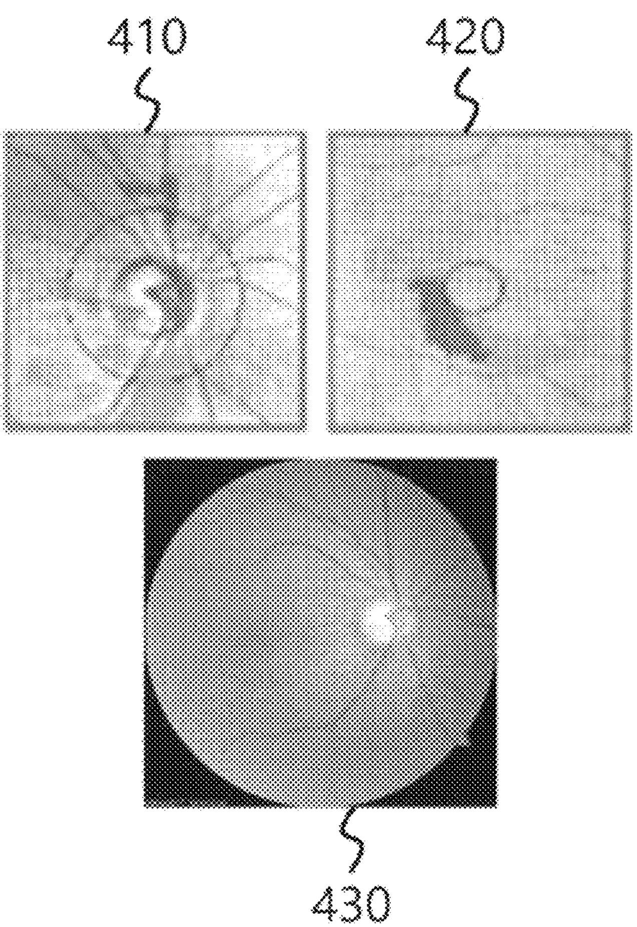
FIG. 4 is a view illustrating a first-$n^{th}$ comparison image and a second-$n^{th}$ comparison image according to an embodiment of the present invention.
Figure 5:
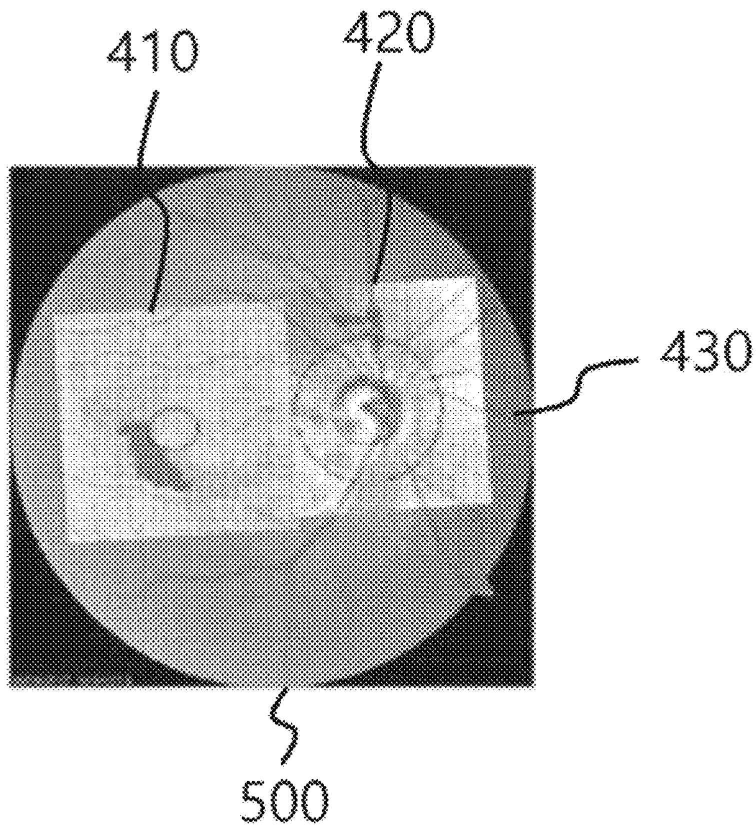
FIG. 5 is a view illustrating an $n^{th}$ eye disease progression image according to an embodiment of the present invention.

FIG. 4 is a view illustrating the first-$n^{th}$ comparison image and the second-$n^{th}$ comparison image according to an embodiment of the present invention, and FIG. 5 is a view illustrating an $n^{th}$ eye disease progression image according to an embodiment of the present invention.

Referring to FIG. 4, a first image 410, a second image 420, and a general fundus image 430 are illustrated.

The first image 410 is an image in which the first-1 comparison image to the first-$n^{th}$ comparison image are combined, and may be an image in which a change in the thickness of an optic nerve near a user's optic disc according to the passage of time is expressed in color. The first image 410 of FIG. 4 is an image in which two first comparison images are combined, wherein an area darker than the background (hereinafter 'dark area') may be an optic nerve damage area generated in the first-1 comparison image, and an area darker than the dark area (hereinafter 'darkest area') may be an optic nerve damage area newly generated in the first-2 comparison images. Accordingly, an administrator may recognize an optic nerve damage sequence of the user's optic disc through the first image 410 at a glance.

The second image 420 is an image in which the second-1 comparison image to the second-$n^{th}$ comparison image are combined, and may be an image in which a change in the thickness of the optic nerve near the user's macula according to the passage of time is expressed in color. The second image 420 of FIG. 4 is an image in which two first comparison images are combined, wherein a dark area may be an optic nerve damage area generated in the second-1 comparison image, and a darkest area may be an optic nerve damage area newly generated in the second-2 comparison images. Accordingly, an administrator may recognize an optic nerve damage sequence of the user's macula through the second image 420 at a glance.

The general fundus image 430 may be a fundus image of a normal person without an eye disease (e.g., glaucoma). Alternatively, the general fundus image 430 is a fundus image for the user, and may be a fundus image generated before the occurrence of an eye disease.

Accordingly, the processor 110 may generate an $n^{th}$ eye disease progression image by combining the first image 410, the second image 420, and the general fundus image 430.

Referring to FIG. 5, an $n^{th}$ eye disease progression image 500 generated by the processor 110 by combining the first image 410, the second image 420, and the general fundus image 430 is illustrated. The processor 110 may detect an optic disc portion (indicated by a circle in FIG. 4) and a blood vessel portion of the first image 410. In addition, the processor 110 may detect a blood vessel portion from the second image 420. In addition, the processor 110 may detect an optic disc portion and a blood vessel portion in the general fundus image 430. Accordingly, as illustrated in FIG. 5, the processor 110 may generate the $n^{th}$ eye disease progression image 500 by matching the optic disc portion and the blood vessel portion.

Accordingly, through the $n^{th}$ eye disease progression image 500, the administrator may recognize at a glance the transformation of an optic nerve damage portion according to the progression of the user's eye disease (glaucoma) and the structural relationship between the optic nerve damage at the optic disc and the optic nerve damage at the macula.

Referring back to FIG. 2, in operation S250, the processor 110 may generate the $n^{th}$ eye disease image by combining the $n^{th}$ eye disease progression image 500 and the prone area image previously stored in the memory 130. The $n^{th}$ eye disease image will be described later with reference to FIGS. 6 and 7.

Figure 6:
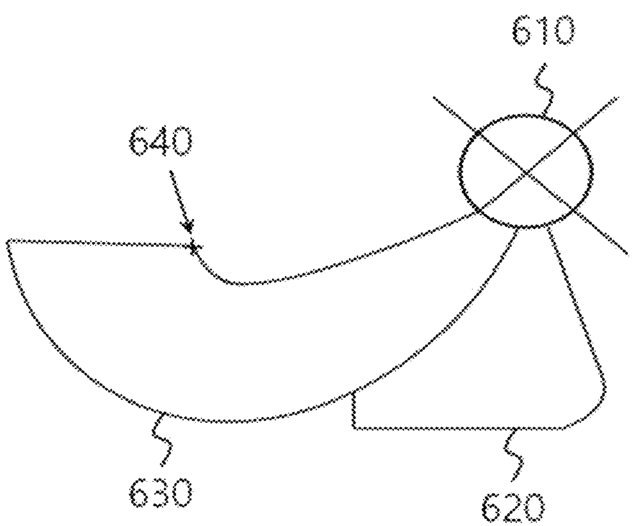
FIG. 6 is a view of a prone area image according to an embodiment of the present invention.
Figure 7:
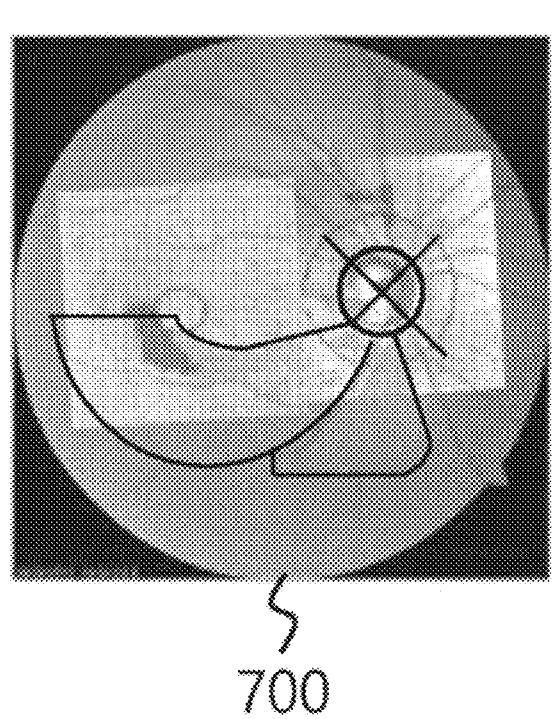
FIG. 7 is a view of an $n^{th}$ eye disease image according to an embodiment of the present invention.

FIG. 6 is a view of a prone area image according to an embodiment of the present invention, and FIG. 7 is a view of an $n^{th}$ eye disease image according to an embodiment of the present invention.

A prone area image 600 illustrated in FIG. 6 is an image previously stored in the memory 130, and may be an image of an area in which optic nerve damage frequently occurs according to the occurrence of, for example, an eye disease. In other words, the prone area image 600 may include a first area 610 corresponding to the optic disc, a second area 620 in which damage to the optic nerve is frequently observed in the optic disc, and a third area 630 in which damage to the optic nerve is frequently observed in the macular area.

Accordingly, as illustrated in FIG. 7, the processor 110 may generate an $n^{th}$ eye disease image 700 by combining the $n^{th}$ eye disease progression image 500 and the frequent area image 600. For example, the processor 110 may generate the $n^{th}$ eye disease image 700 by matching the first area 610 of the prone area image 600 with the optic disc of the $n^{th}$ eye disease progression image, and matching a macular center point 640 of the second area 620 of the prone area image 600 with the macular center (a circular area of the second image 420) of the $n^{th}$ eye disease progression image.

Accordingly, the administrator may recognize at a glance whether the user's eye disease (glaucoma) progression is general progression corresponding to a prone area through the $n^{th}$ eye disease image 700.

Figure 3:
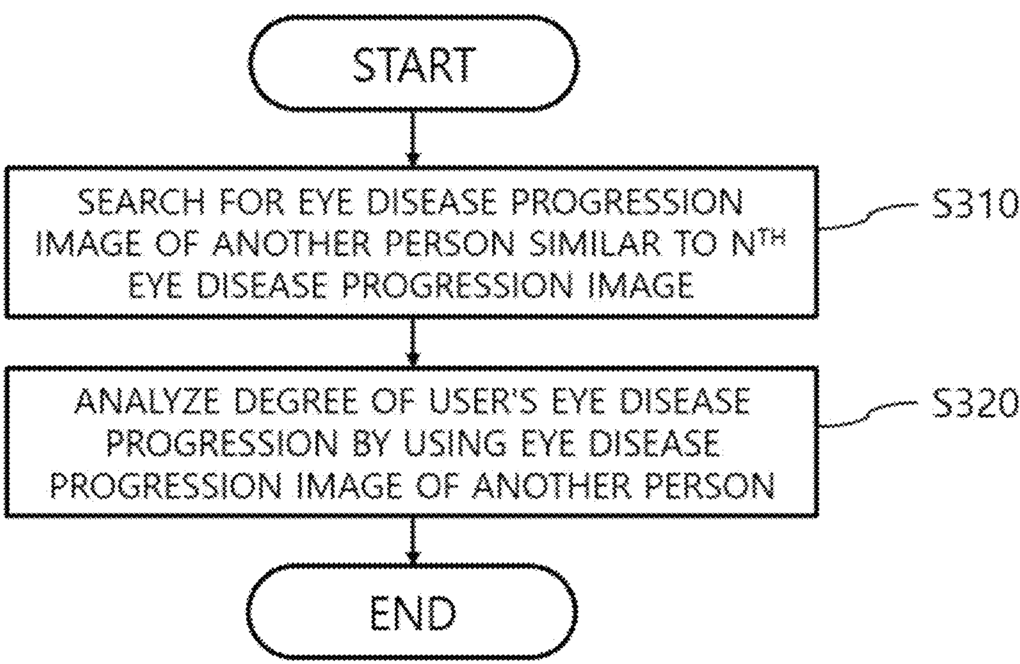
FIG. 3 is a flowchart illustrating a method of analyzing user's eye disease progression information according to an embodiment of the present invention.

FIG. 3 is a flowchart illustrating a method of analyzing user's eye disease progression information according to an embodiment of the present invention.

In operation S310, the processor 110 may search for an eye disease progression image of another person similar to the $n^{th}$ eye disease progression image 500.

For example, all of eye disease progression images corresponding to a plurality of users may be stored in the memory 130. In this case, the processor 110 may search for an eye disease progression image of another person corresponding to the $n^{th}$ eye disease progression image 500 considering a generation period and an optic nerve change position corresponding to the $n^{th}$ eye disease progression image 500.

The generation period may correspond to a time from when a first eye disease progression image is generated to a time when the $n^{th}$ eye disease progression image 500 is generated.

In addition, the optic nerve change position may correspond to optic nerve change positions displayed in a first combined image to the $n^{th}$ combined image, and an optic nerve change position displayed in a second eye disease progression image to an optic nerve change position displayed in the $n^{th}$ eye disease progression image 500.

Accordingly, the processor 110 may detect a first time at which the first eye disease progression image is generated and a first optic nerve change position corresponding to the optic nerve change position, may detect a second time at which the second eye disease progression image is generated and a second optic nerve change position corresponding to the optic nerve change position, and may detect an $n^{th}$ time at which the $n^{th}$ eye disease progression image is generated and an $n^{th}$ optic nerve change position corresponding to the optic nerve change position.

In addition, the processor 110 may search the memory 130 for an eye disease progression image of another person in which the first time, the first optic nerve change position, the second time, the second optic nerve change position, the $n^{th}$ time, and the $n^{th}$ optic nerve change position all match, and may read the eye disease progression image of another person.

For another example, eye disease progression images corresponding to a plurality of users are all stored in an external server (not shown), and after the external server (not shown) is connected to a communication modem 120 to receive the $n^{th}$ eye disease progression image 500, a corresponding eye disease progression image of another person may be read. The external server (not shown) may transmit the read eye disease progression image of another person to the communication modem 120, and the communication modem 120 may output the eye disease progression image of another person to the processor 110.

In operation S320, the processor 110 may analyze the degree of the user's eye disease progression by using the eye disease progression image of another person. The eye disease progression image of another person is for a case in which the degree of eye disease progression of another person is more severe than the degree of the user's eye disease progression, and may be an eye disease progression image corresponding to a case of already blindness. Accordingly, the processor 110 may be able to recognize which portion of the optic nerve is highly likely to be damaged in the future by comparing the eye disease progression image of another person with the $n^{th}$ eye disease progression image 500 of the user. Through this, the processor 110 may analyze the percentage of the user's eye disease progression to blindness, and the like.

Figure 8:
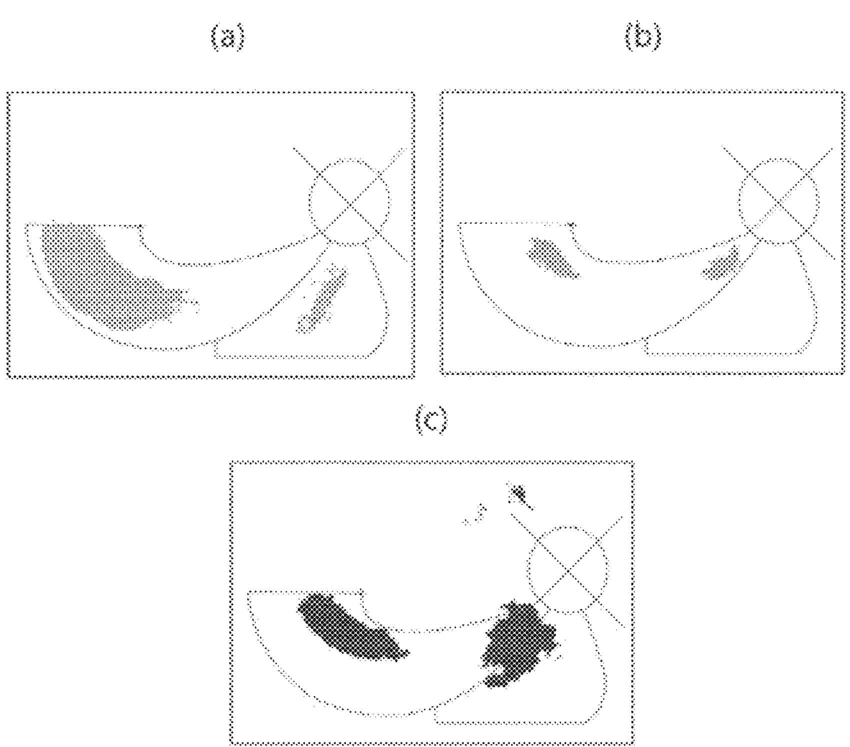
FIG. 8 is a view illustrating a case in which combined images are schematically transformed according to an embodiment of the present invention.

FIG. 8 is a view illustrating a case in which combined images are schematically transformed according to an embodiment of the present invention.

Drawings illustrated in FIG. 8 are schematically converted images of a first combined image (FIG. 8(*a*)), a second combined image (FIG. 8(*b*)), and a third combined image (FIG. 8(*c*)), and may each correspond to an image in which a fundus image portion is removed from each of the combined images.

Accordingly, an administrator will be able to clearly recognize a change in a user's optic nerve through a schematically transformed image of each eye disease.

Hereinabove, the present invention has been described with reference to the preferred embodiments. However, it will be appreciated by one of ordinary skill in the art that various modifications and changes of the present invention can be made without departing from the spirit and the scope of the inventive concept which are defined in the appended claims and their equivalents.

The invention claimed is:

1. A device for determining structural progression of an eye disease, the device comprising:
- a processor; and
- a memory electrically connected to the processor,
- wherein, when the processor is executed, the memory stores instructions for:
  - obtaining a first-$n^{th}$ ocular image, which is an $n^{th}$ first ocular image for a user (where n is a natural number),
  - obtaining a second-$n^{th}$ ocular image, which is an $n^{th}$ second ocular image for the user,
  - combining the first-$n^{th}$ ocular image and the second-$n^{th}$ ocular image according to a preset method to generate an $n^{th}$ combined image, and
  - generating an $n^{th}$ eye disease image for the user by using the $n^{th}$ combined image and a preset prone area image,
- wherein the first-$n^{th}$ ocular image is an ocular image of the user's optic disc,
- wherein the second-$n^{th}$ ocular image is an ocular image of the user's macula, and
- wherein the preset prone area image includes a first area corresponding to the optic disc, a second area where optic nerve damage is observed in the optic disc, and a third area where the optic nerve damage is observed in the macular area.

2. The device of claim 1, wherein the memory stores instructions for generating a first-$n^{th}$ comparison image by using an optic nerve thickness of the first-$n^{th}$ ocular image and a pre-stored first-$(n-1)^{th}$ ocular image, generating a second-$n^{th}$ comparison image by using an optic nerve thickness of the second-$n^{th}$ ocular image and a pre-stored second-$(n-1)^{th}$ ocular image, and generating the $n^{th}$ combined image by combining the first-$n^{th}$ comparison image and the second-$n^{th}$ comparison image according to a preset method.

3. The device of claim 2, wherein the memory stores instructions for generating the $n^{th}$ combined image by matching a blood vessel portion of the first-$n^{th}$ comparison image and a blood vessel portion of the second-$n^{th}$ comparison image.

4. The device of claim 1, wherein the memory stores instructions for generating an $n^{th}$ eye disease progression image for the user using pre-stored first to n−1 combined images and the $n^{th}$ combined image, and generating the $n^{th}$ eye disease image by combining the $n^{th}$ eye disease progression image and the prone area image.

5. The device of claim 4, wherein the memory stores instructions for, when an eye disease progression image of another person corresponding to the $n^{th}$ eye disease progression image is searched, analyzing the degree of eye disease progression of the user using the eye disease progression image of another person.

6. The device of claim 5, wherein the memory stores instructions for searching for the eye disease progression image of another person considering a generation period and an optic nerve change position corresponding to the $n^{th}$ eye disease image,
- wherein the generation period corresponds to a generation period of a first eye disease image to the $n^{th}$ eye disease image,
- wherein the optic nerve change position corresponds to an optic nerve change position of each of a first combined image to the $n^{th}$ combined image,
- wherein the first eye disease image is a first image of eye disease of the user, and
- wherein the first combined image is a first combined image of the user.

7. A method of determining structural progression of an eye disease performed in a device for determining structural progression of an eye disease, the method comprising:
- obtaining a first-$n^{th}$ ocular image, which is an $n^{th}$ first ocular image for a user (where n is a natural number);
- obtaining a second-$n^{th}$ ocular image, which is an $n^{th}$ second ocular image for the user;
- generating an $n^{th}$ combined image by combining the first-$n^{th}$ ocular image and the second-$n^{th}$ ocular image according to a preset method; and
- generating an $n^{th}$ eye disease image for the user by using the $n^{th}$ combined image and a preset prone area images,
- wherein the first-$n^{th}$ ocular image is an ocular image of the user's optic disc,
- wherein the second-$n^{th}$ ocular image is an ocular image of the user's macula, and
- wherein the preset prone area image includes a first area corresponding to the optic disc, a second area where optic nerve damage is observed in the optic disc, and a third area where the optic nerve damage is observed in the macular area.

8. The method of claim 7, wherein the generating of the $n^{th}$ combined image comprises:
- generating a first-$n^{th}$ comparison image by using an optic nerve thickness of the first-$n^{th}$ ocular image and a pre-stored first-(n−1) th ocular image;
- generating a second-$n^{th}$ comparison image by using an optic nerve thickness of the second-$n^{th}$ ocular image and a pre-stored second-(n−1) th ocular image; and
- generating the $n^{th}$ combined image by combining the first-$n^{th}$ comparison image and the second-$n^{th}$ comparison image according to a preset method.

9. The method of claim 8, wherein the generating of the $n^{th}$ combined image comprise generating the $n^{th}$ combined image by matching a blood vessel portion of the first-$n^{th}$ comparison image and a blood vessel portion of the second-$n^{th}$ comparison image.

10. The method of claim 7, wherein the generating of the $n^{th}$ eye disease image comprises:
- generating an $n^{th}$ eye disease progression image for the user using pre-stored first to n−1 combined images and the $n^{th}$ combined image; and generating the $n^{th}$ eye disease image by combining the $n^{th}$ eye disease progression image and the prone area image.

11. The method of claim 10, further comprising, in a case that an eye disease progression image of another person corresponding to the $n^{th}$ eye disease progression image is searched, analyzing the degree of eye disease progression of the user using the eye disease progression image of another person.

12. The method of claim 11, wherein the analyzing of the degree of eye disease progression of the user comprises:

searching for the eye disease progression image of another person considering a generation period and an optic nerve change position corresponding to the $n^{th}$ eye disease progression image, wherein the generation period corresponds to a generation period of a first eye disease progression image to the $n^{th}$ eye disease progression image, wherein the optic nerve change position corresponds to an optic nerve change position of each of a first combined image to the $n^{th}$ combined image, wherein the first eye disease progression image is a first eye disease progression image of the user, and wherein the first combined image is a first combined image of the user.

* * * * *